(12) United States Patent
Cyran et al.

(10) Patent No.: US 9,906,583 B2
(45) Date of Patent: Feb. 27, 2018

(54) SYSTEM AND METHOD FOR AUTOMATICALLY UPLOADING, DOWNLOADING, AND UPDATING DATA SUCH AS SLEEP STUDY DATA

(71) Applicant: KONINKLIJKE PHILIPS N.V., Eindhoven (NL)

(72) Inventors: Robert John Cyran, Delmont, PA (US); Paul David Juozitis, Murrysville, PA (US); Edward Alan Anderson, Gibsonia, PA (US)

(73) Assignee: Koninklijke Philips N.V., Eindhoven (NL)

( * ) Notice: Subject to any disclaimer, the term of this patent is extended or adjusted under 35 U.S.C. 154(b) by 154 days.

(21) Appl. No.: 14/890,182

(22) PCT Filed: May 28, 2014

(86) PCT No.: PCT/IB2014/061767
§ 371 (c)(1),
(2) Date: Nov. 10, 2015

(87) PCT Pub. No.: WO2014/191925
PCT Pub. Date: Dec. 4, 2014

(65) Prior Publication Data
US 2016/0134683 A1 May 12, 2016

Related U.S. Application Data

(60) Provisional application No. 61/829,306, filed on May 31, 2013.

(51) Int. Cl.
| G06F 15/16 | (2006.01) |
| H04L 29/08 | (2006.01) |
| G06F 19/00 | (2018.01) |
| G06F 17/30 | (2006.01) |
| H04L 29/06 | (2006.01) |

(52) U.S. Cl.
CPC ........ H04L 67/06 (2013.01); G06F 17/30979 (2013.01); G06F 19/322 (2013.01); H04L 67/1095 (2013.01); H04L 67/34 (2013.01); H04L 67/42 (2013.01)

(58) Field of Classification Search
CPC ......... H04L 67/06; H04L 67/34; H04L 67/42; H04L 67/1095; G06F 17/30979; G06F 19/322
See application file for complete search history.

(56) References Cited

U.S. PATENT DOCUMENTS

| 6,195,678 B1 | 2/2001 | Komuro | |
| 2005/0141312 A1* | 6/2005 | Sinclair | ............... G06F 11/1072 365/222 |
| 2008/0098006 A1* | 4/2008 | Pedersen | ............. H04L 67/1095 |

(Continued)

Primary Examiner — Jonathan Bui

(57) ABSTRACT

A method of automatically transferring data between a client (20) and a server (32), the method including receiving a request to open a set of data at the client, determining whether the set of data exists at the client, if the set of data does not exist at the client, downloading the set of data from the server, otherwise checking for updates to the set of data on the server and downloading any new or updated files in the set of data from the server, and opening the set of data at the client.

16 Claims, 7 Drawing Sheets

(56) References Cited

U.S. PATENT DOCUMENTS

| | | | | |
|---|---|---|---|---|
| 2008/0205608 | A1* | 8/2008 | Tal | H04M 3/527 379/93.01 |
| 2010/0011415 | A1* | 1/2010 | Cortes | G06Q 30/06 726/4 |
| 2010/0228834 | A1* | 9/2010 | Hung | G06F 17/3056 709/217 |
| 2010/0266263 | A1* | 10/2010 | Murakami | G11B 27/002 386/263 |
| 2010/0274816 | A1* | 10/2010 | Guzik | G11B 27/034 707/802 |
| 2011/0055721 | A1* | 3/2011 | Jain | G06Q 30/02 715/748 |
| 2011/0208631 | A1* | 8/2011 | Glick | G06Q 40/02 705/35 |
| 2011/0217021 | A1* | 9/2011 | Dubin | H04N 7/147 386/278 |
| 2011/0314229 | A1* | 12/2011 | Miller | G06F 11/1435 711/154 |
| 2012/0203739 | A1* | 8/2012 | Soundararajan | G06F 9/5077 707/639 |
| 2013/0185346 | A1* | 7/2013 | Lee | H04L 67/02 709/201 |
| 2013/0282816 | A1* | 10/2013 | Fujita | H04L 67/02 709/204 |
| 2014/0059273 | A1* | 2/2014 | Fujimoto | G06F 12/0246 711/103 |
| 2014/0173230 | A1* | 6/2014 | Smith | H04L 67/1095 711/162 |

\* cited by examiner

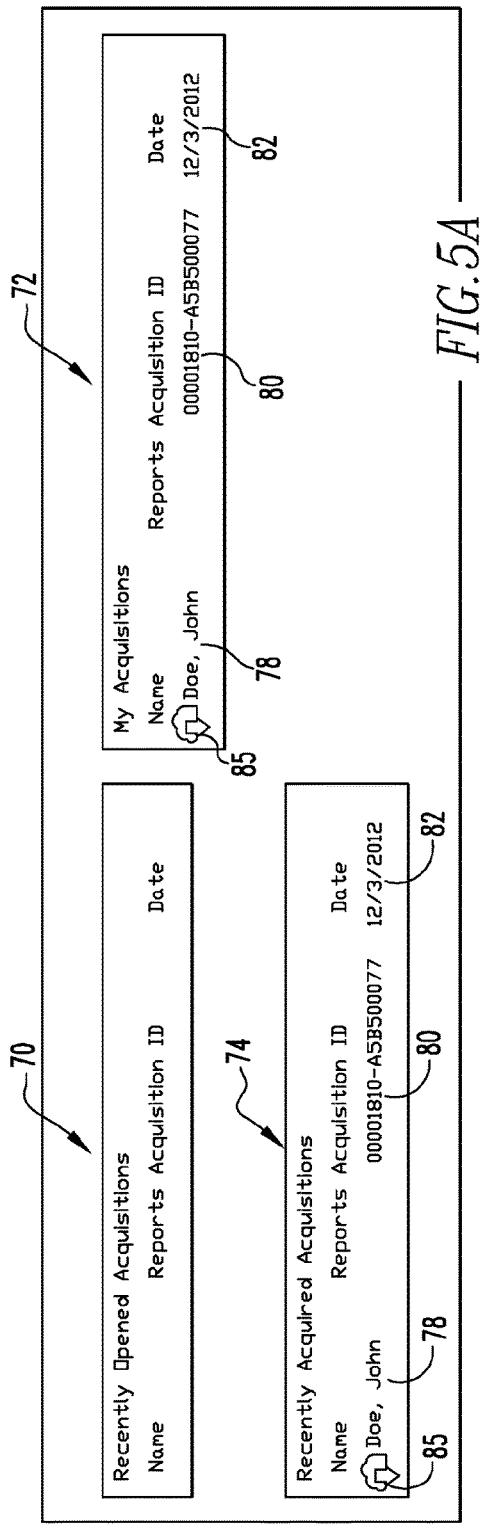
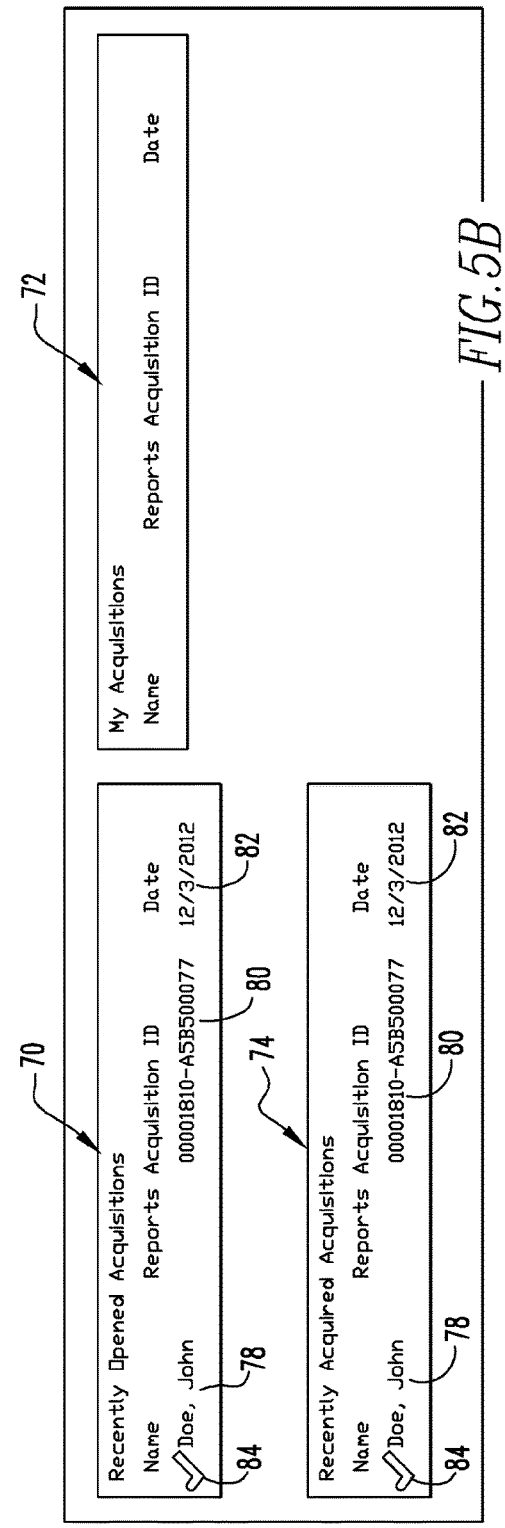
FIG. 5A
FIG. 5B

FIG. 9

SYSTEM AND METHOD FOR AUTOMATICALLY UPLOADING, DOWNLOADING, AND UPDATING DATA SUCH AS SLEEP STUDY DATA

CROSS-REFERENCE TO PRIOR APPLICATIONS

This application is the U.S. National Phase application under 35 U.S.C. § 371 of International Application Serial No. PCT/IB2014/061767, filed on May 28, 2014, which claims the benefit of U.S. Application Ser. No. 61/829,306, filed on May 31, 2013. These applications are hereby incorporated by reference herein.

BACKGROUND OF THE INVENTION

1. Field of the Invention

The present invention pertains to transferring data, and, in particular, to a system and method for automatically uploading, downloading, and updating sleep study data.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Various methods have been used to assess whether a patient suffers from OSA. The most comprehensive method is a clinical polysomnogram (PSG), which can diagnose many significant sleep pathologies. A PSG generally involves a sleep study of a patient where audio and other parameters of the patient is recorded while the patient sleeps. A technician then "scores" the recorded data. Scoring the recorded data involves analyzing the data to identify events that occurred during the PSG that may be useful in diagnosing sleep pathologies. Data collected during a PSG is generally stored in several different files such as multiple audio files, other data files, and a scoring file.

The PSG data (also referred to as sleep study data) is generated or used in several different locations, such as a sleep lab, a scoring technician's office, and a physician's office. It is preferable to store the PSG at a central location, such as a server, where it is accessible to multiple locations through a network, such as the internet.

The PSG is generated and updated at several locations, which necessitates transferring and updating files between the remote locations and the central location to ensure that the PSG data being accessed by a user is up to date. A file transfer protocol (FTP) server on a server at the central location has been used to download and upload PSG data between the central location and the remote locations. Other file sharing systems have also been used to manage file transfers between the central location and the remote locations. However, these file transfer mechanisms require users to manually initiate downloads or uploads. For example, if a scoring technician wants to score a sleep study, he must first download the sleep study files from the central location to his remote location. Then, the scoring technician scores the sleep study data on a computer at his remote location. Finally, the scoring technician uploads any new or updated files to the central location.

This process can quickly become cumbersome as even a single study may need to be accessed and updated multiple times before a patient is diagnosed. Moreover, it may be difficult for a user to determine which, if any, sleep study files have been updated at the central location.

Current file transfer services upload to a temporary directory on the server, and when the upload is complete, the file is copied to a permanent directory. This protocol prevents an incomplete transfer of a single file, such as one in which connection was lost before the upload completed, from being permanently stored on the server. Some file transfer services forgo the temporary directory and copy files directly to their final destination. However, this process can lead to incomplete files being stored at their final destination in the case of an incomplete transfer.

Additionally, when a file is being uploaded, the server will provide synchronization locking which prevents the same file from being uploaded or downloaded by a different user at the same time. However, under current file transfer protocols, uploads are transferred to a permanent directory and synchronization locking is provided on a file-by-file basis. That is, when uploading of one file is complete, the file will be transferred to the permanent directory and the synchronization locking will stop.

Current file transfer services behave in a similar manner when downloading files from the server to a client computer. That is, they may download a file to a temporary directory to prevent an incomplete file from being downloaded to its final destination directory in the case the connection was lost before the download was complete. Some services may download a file directly to its final destination directory, which can result in an incomplete transfer. Additionally, when a file is being downloaded, the client operating system will provide synchronization locking which prevents other applications on the client from accessing the file while it is being downloaded. However, under current file transfer protocols the synchronization locking is provided on a file-by-file basis.

Accordingly, a need exists for improvement in transferring data files such as sleep study data files between central and remote locations.

SUMMARY OF THE INVENTION

In one embodiment, a method of automatically transferring data between a client and a server includes receiving a request to open a set of data at the client, determining whether the set of data exists at the client, if the set of data does not exist at the client, downloading the set of data from the server, otherwise checking for updates to the set of data on the server and downloading any new or updated files in the set of data from the server, and opening the set of data at the client.

In another embodiment, a method of automatically transferring data between a client and a server includes receiving a request to close a set of data at the client, determining whether the set of data includes new or updated files, upon determining that the set of data includes new or updated files, determining whether a network connection to the server is available, if the network connection is available, uploading new and updated files to the server, otherwise displaying a notification that new and updated files have not been uploaded, and closing the set of data.

In another embodiment, a non-transitory computer readable medium storing one or more programs, including instructions, which when executed by a computer, causes the computer to perform a method of transferring data between a client and a server, the method including receiving a request to open a set of data at the client, determining whether the set of data exists at the client, if the set of data does not exist at the client, downloading the set of data from the server, otherwise checking for updates to the set of data on the server and downloading any new or updated files in the set of data from the server, and opening the set of data at the client.

In another embodiment, a non-transitory computer readable medium storing one or more programs, including instructions, which when executed by a computer, causes the computer to perform a method of transferring data between a client and a server, the method including receiving a request to close a set of data at the client, determining whether the set of data includes new or updated files, upon determining that the set of data includes new or updated files, determining whether a network connection to the server is available, if the network connection is available, uploading new and updated files to the server, otherwise displaying a notification that new and updated files have not been uploaded, and closing the set of data.

In another embodiment, a system to automatically transfer data includes a client device structured to receive a request to open a set of data and to determine whether the set of data exists on the client device, and to open the data, wherein the client device is structured to download the set of data from a server prior to opening the set of data, if the client device determines the set of data does not exist on the client device, and wherein the client device is structured to check for updates to the set of data and to download any new or updated files in the set of data from the server prior to opening the set of data, if the client device determines that the set of data does exist on the client device.

In another embodiment, a system to automatically transfer data includes a client device structured to receive a request to close a set of data, to determine whether the set of data includes new or updated files, and to close the set of data, wherein the client is structured to determine whether a network connection is available upon determining that the set of data includes new or updated files, wherein the client device is structured to upload new and updated files to a server prior to closing the set of data if the network connection is available, and wherein the client device is structured to display a notification that new and updated files have not been uploaded prior to closing the set of data if the network connection is not available.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 5A and 5B are view of screenshots of a user interface for opening and closing sleep studies according to one exemplary embodiment of the disclosed concept;

FIG. 9 is a view of a user interface for manually uploading or downloading sleep study data according to one exemplary embodiment of the disclosed concept.

DETAILED DESCRIPTION OF EXEMPLARY EMBODIMENTS

Figure 1:
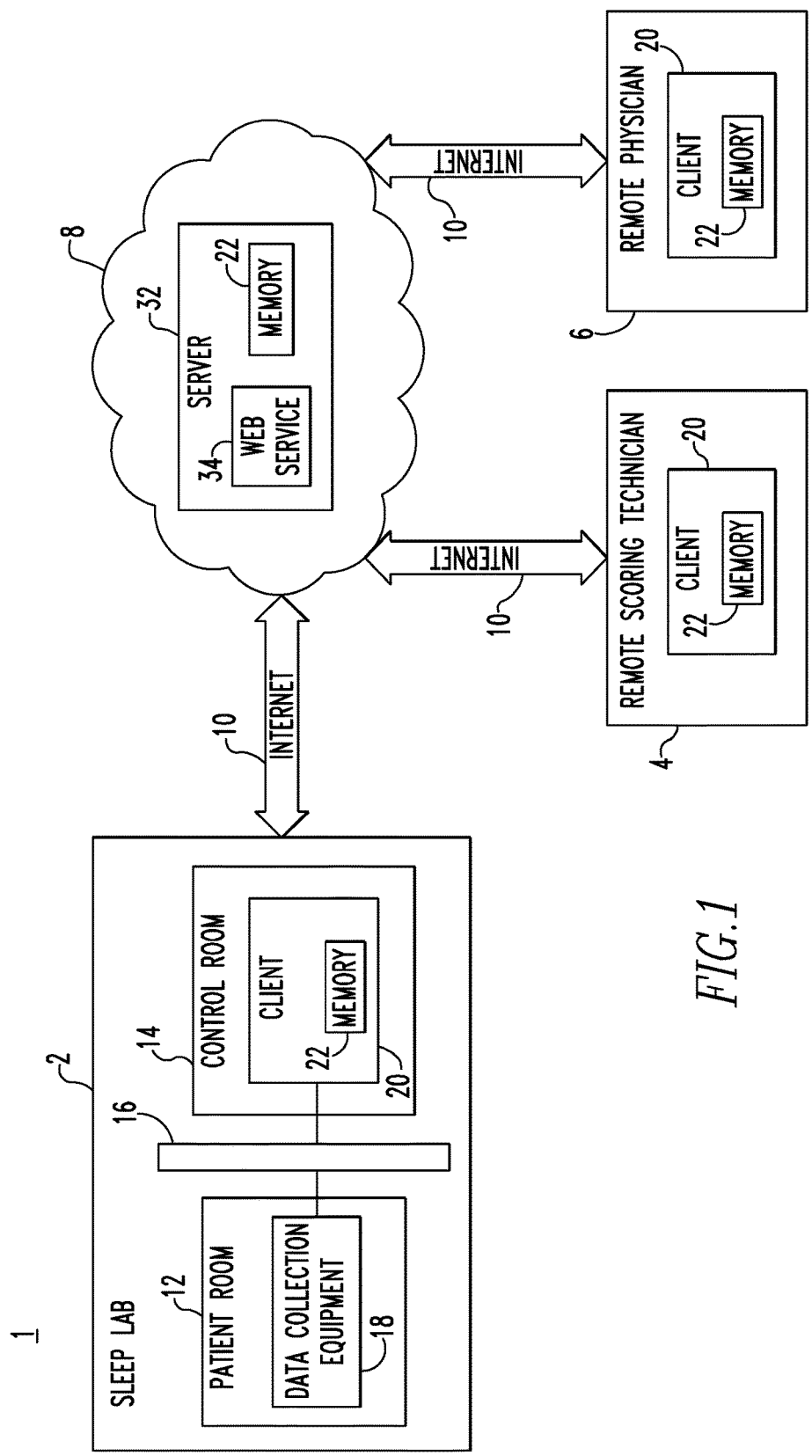
FIG. 1 is a schematic view of a system adapted to collect and store PSG data in a centralized location according to one exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 1 adapted to collect and store sleep study data is generally shown in FIG. 1. System 1 is distributed over several locations including a sleep lab 2, a remote scoring technician site 4, a remote physician site 6, and a central server site 8. Central server site 8 includes a server 32 and each of sleep lab 2, remote scoring technician site 4, and remote physician site 6 include a client 20. Clients 20 are each communicatively connected to server 32 by suitable network connections such as internet connections 10.

Clients 20 are any suitable processing device such as, without limitation, a general-purpose computer, a wireless device, a personal computer, or a mobile phone. Clients 20 and server 32 each include an associated memory 22. Memory 22 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 22 may also be located outside of clients 20 or server 32 and communicatively connected with its associated client 20 or server 32. Memory 22 may also be a removable device that is able to be removed from its associated client 20 or server 32.

Sleep lab 2 includes a patient room 12 and a control room 14. Patient room 12 and control room 14 are communicatively connected by a suitable network connection such as a local area network connection 16. Patient room 12 includes data collection equipment 18. Data collection equipment 18 is used to collect raw sleep study data such, without limitation, audio and video data, electroencephalogram (EEG) data, electrocardiogram (ECG) data, electroculogram (EOG) data, electromyogram (EMG) data, measurements of nasal airflow, measurements of blood oxygen levels and/or other physiological parameters. Control room 14 includes client 20 and memory 22. The raw sleep study data is transferred from data collection equipment 18 to client 20 via local area network connection 16 and is stored in memory 22. The raw sleep study data is stored in memory 22 as a set of files.

Remote scoring technician site 4 includes its associated client 20 and memory 22. A scoring technician at remote scoring technician site 4 "scores" raw sleep study data and stores the scoring data in memory 22 as a file. The scoring data includes data such as, without limitation, sleep staging data, apnea event data, and high heart rate event data.

Remote physician site 6 includes its associated client 20 and memory 22. A physician at remote physician site 6 reviews the raw sleep study data and scoring data in order to diagnose a patient.

Central server site 8 includes server 32 which is communicatively connected with clients 20 in order to send or receive data. Server 32 includes memory 22 which stores the data. Server 32 also includes web service 34. Web service 34 coordinates communication between server 32 and clients 20 such as responding to requests from clients 20 for data uploads or downloads. Server 32 is structured to centrally store sleep study data where it can be downloaded or updated by any of clients 20.

Although sleep lab 2, remote scoring technician site 4 and remote physician site 6 are shown in FIG. 1, it will be appreciated that any suitable remote sites may be adapted to access sleep study data at central server site 8 without departing from the scope of the disclosed concept.

Figure 2:
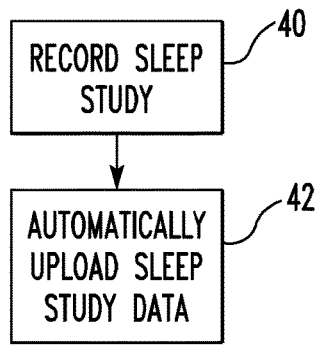
FIG. 2 is a flowchart of a method of automatically uploading sleep study data according to one exemplary embodiment of the disclosed concept.

A flowchart of a method of automatically uploading sleep study files to server 32 in accordance with an exemplary embodiment of the disclosed concept is shown in FIG. 2. At 40, raw sleep study data is recorded and saved to client 20. When the sleep study is completed and all the sleep study files are saved to client 20, client 20 automatically uploads the sleep study files to server 32 at 42. A user does not need to manually initiate uploading of the sleep study files.

Figure 3:
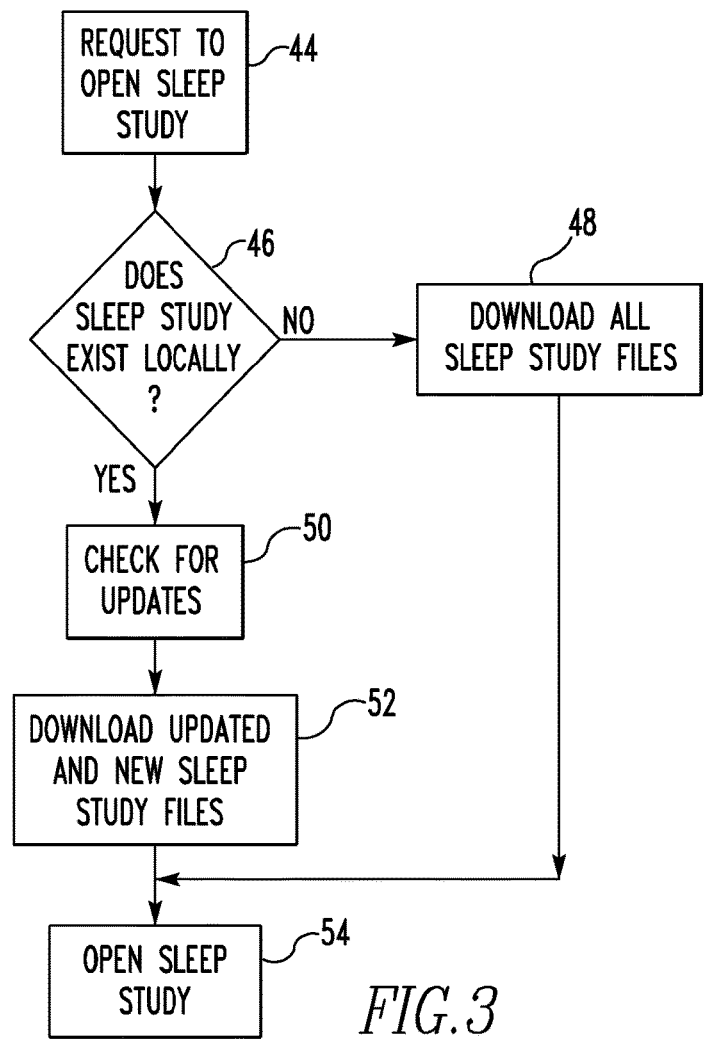
FIG. 3 is a flowchart of a method of automatically downloading sleep study data according to one exemplary embodiment of the disclosed concept.

A flowchart of a method of automatically downloading new and updated sleep study files to client 20 in accordance with an exemplary embodiment of the disclosed concept is shown in FIG. 3. The method of FIG. 3 begins at 44 when a user requests to open a sleep study at one of clients 20. Upon receiving the request to open the sleep study, client 20 checks if the sleep study files exist locally at 46 (e.g., client 20 checks whether the sleep study files are stored in the memory 22 corresponding to client 20). If the sleep study files do not exist locally, client 20 downloads all files corresponding to the sleep study at 48. If the sleep study files do exist locally, client 20 checks whether the local sleep study files need to be updated at 50. That is, client 20 checks if the local version of the sleep study files is the same as the version of the sleep study files stored on server 32.

At 52, client 20 downloads any new or updated sleep study files. By only downloading new and updated files, downloading the entire sleep study can be avoided when only some of the sleep study files are new or updated. Additionally, by checking for updates, the user is ensured that the local version of the sleep study files is up to date with the version of the sleep study files stored at server 32. Finally, at 54 the sleep study is opened.

It is contemplated that client 20 may check if a network connection to server 32 is available prior to downloading the sleep study files at 48. If the network connection is not available at this point, client 20 may display a notification information the user that the sleep study cannot be opened. Client 20 may also check if a network connection to server 32 is available before downloading new and/or updated sleep study files at 52. If the network connection is not available at this point, client 20 may proceed to open the sleep study and display a notification that the sleep study may be out of date because updates could not be downloaded to client 20.

Figure 4:
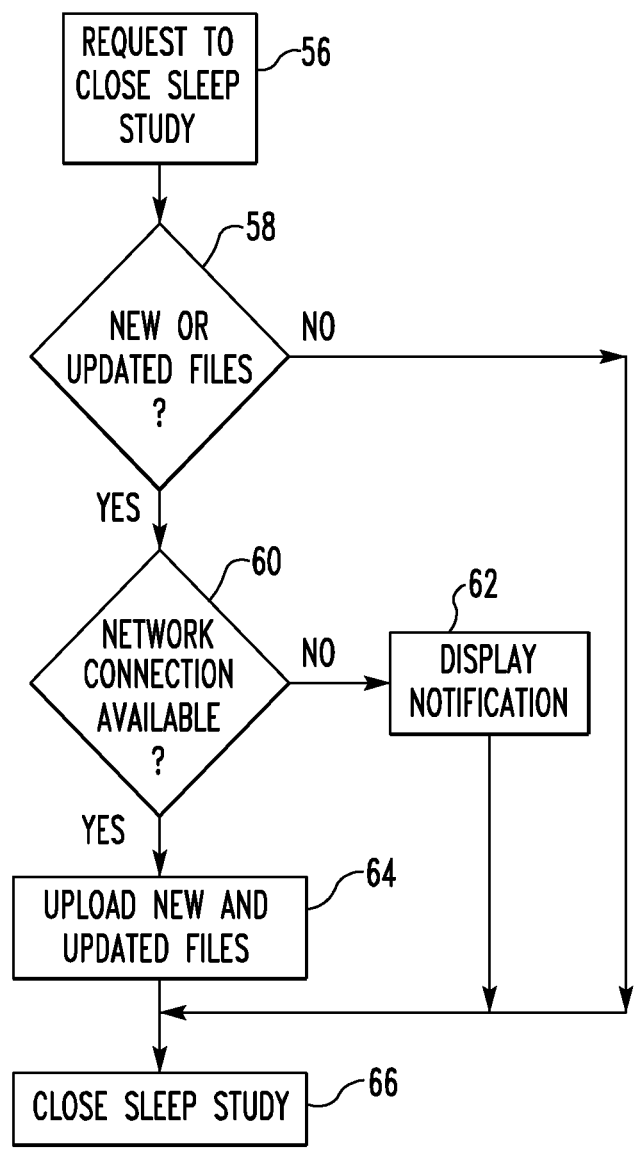
FIG. 4 is a flowchart of a method of automatically updating and uploading sleep study data according to one exemplary embodiment of the disclosed concept.

A flowchart of a method of automatically uploading new and updated sleep study files in accordance with an exemplary embodiment of the disclosed concept is shown in FIG. 4. The method of FIG. 4 begins at 56 when a user requests to close a sleep study at one of clients 20. Upon receiving the request to close the sleep study, client 20 checks if any of the locally stored sleep study files are new or have been updated at 58. That is, client 20 checks if any of the locally stored sleep study files are now different that the sleep study files stored at server 32. If the locally stored sleep study files are not new or updated, client 20 proceed to 66 and closes the sleep study. If the locally stored sleep study files are new or updated, client 20 proceeds to 60 and checks if a network connection is available.

Although client 20 will try to upload new and updated sleep study files automatically, situations will arise where client 20 lacks a network connection and cannot communicate with server 32. In these instances, it is beneficial to inform the user that new or updated sleep study files could not be automatically uploaded to server 32. Thus, if client 20 determines that a network connection is not available at 60, client 20 proceeds to 62 and displays a notification. Notification may inform the user that new and updated sleep study files are not able to be uploaded and also remind the user that the new and updated sleep study files will need to be uploaded. Client 20 then proceeds to 66 and closes the sleep study.

If client 20 determines that a network connection is available, client 20 proceeds to 64 and uploads the new and updated sleep study files to server 32 at 64. By automatically uploading new and updated sleep study files upon closing the sleep study, the process of uploading updated files is largely automated. Furthermore, the sleep study files stored at server 32 are kept up to date and the number of files transferred is limited to those necessary to keep the files stored at server 32 up to date.

FIGS. 5A and 5B are views of a user interface for opening sleep studies in accordance with an exemplary embodiment of the disclosed concept. User interface includes three columns 70, 72, 74 corresponding to different statuses of acquisitions. In the user interface, sleep studies are referred to as acquisitions. The first column 70 lists sleep studies that have recently been opened. The second column 72 lists sleep studies that have been assigned to the user. The third column 74 lists sleep studies that have recently been acquired (i.e., recently recorded).

Each column 70, 72, 74 includes several sub-columns corresponding to information about the sleep studies. The information includes, without limitation, an indicator 76 that identifies the status of the sleep study, the name of the user 78, the acquisition ID 80 (e.g., the ID assigned to the sleep study), and the date 82.

Figure 6:
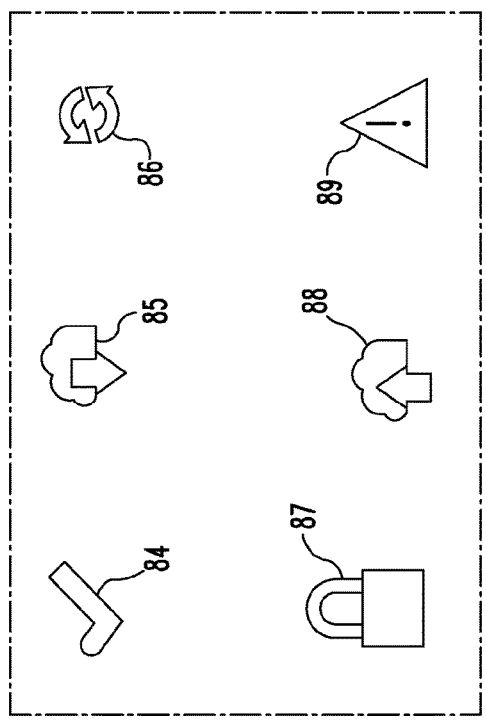
FIG. 6 shows various indicators used with the user interface of FIGS. 5A and 5B.

Indicator 76 may be an icon or other type of identifier that indicates the status of the sleep study. Six examples of indicators 84, 85, 86, 87, 88, 89 representing different statuses are shown in FIG. 6. Check indicator 84 (shown also in FIG. 5B) indicates that the sleep study files are stored both locally at client 20 and remotely at server 32 and that the sleep study files at client 20 and server 32 are synchronized with each other. Cloud download indicator 85 indicates that the sleep study is stored remotely on server 32, but not locally at client 20. Synchronize indicator 86 (also shown in FIG. 7) indicates that the sleep study files are stored both locally at client 20 and remotely at server 32, but that the sleep study files at client 20 and server 32 need to be synchronized. Different colors may be used for synchronize indicator 86 such as using red to indicate that the remote copy of sleep study has been updated or yellow to indicate that the local copy of the sleep study has been updated. Lock indicator 87 indicates that the sleep study is locked and inaccessible (i.e., the sleep study is opened by another user at the current site or a remote site, and is inaccessible). Locks are automatically removed when the sleep study is closed. Different colors may be used for lock indicator 87 such as using red to indicate that the sleep study is locked by another user and yellow to indicate that the sleep study is locked by the current user. Upload cloud indicator 88 indicates that the sleep study files are stored locally at client 20, but are not stored remotely on server 32. Warning indicator 89 indicates that local and remote versions of sleep study are in conflict. This may happen when a local copy of the sleep study is updated when no network connection is available, and during that time, the remote copy of the sleep study is update by another user. Although some examples of indicators are shown in FIG. 6, it will be appreciated by those having ordinary skill in the art that the aesthetic characteristics of the indicators may be changed without departing from the scope of the disclosed concept.

Referring to FIG. 5A, cloud download indicator 85 indicates that the sleep study files are stored on server 32, but are not stored on client 20. By clicking on the sleep study to open it, the method of FIG. 3 is initiated. Once the method of FIG. 3 has run and the sleep study files have been downloaded and the sleep study is opened, cloud download indicator 85 is changed to check indicator 84, as shown in FIG. 5B. As previously described, check indicator 84 indicates that the sleep study files are stored both locally at client 20 and remotely at server 32 and that both the locally and remotely stored sleep study files are synchronized. Additionally, the sleep study is moved from the second column 72 to the first column 70 since it has been recently opened.

Figure 7:
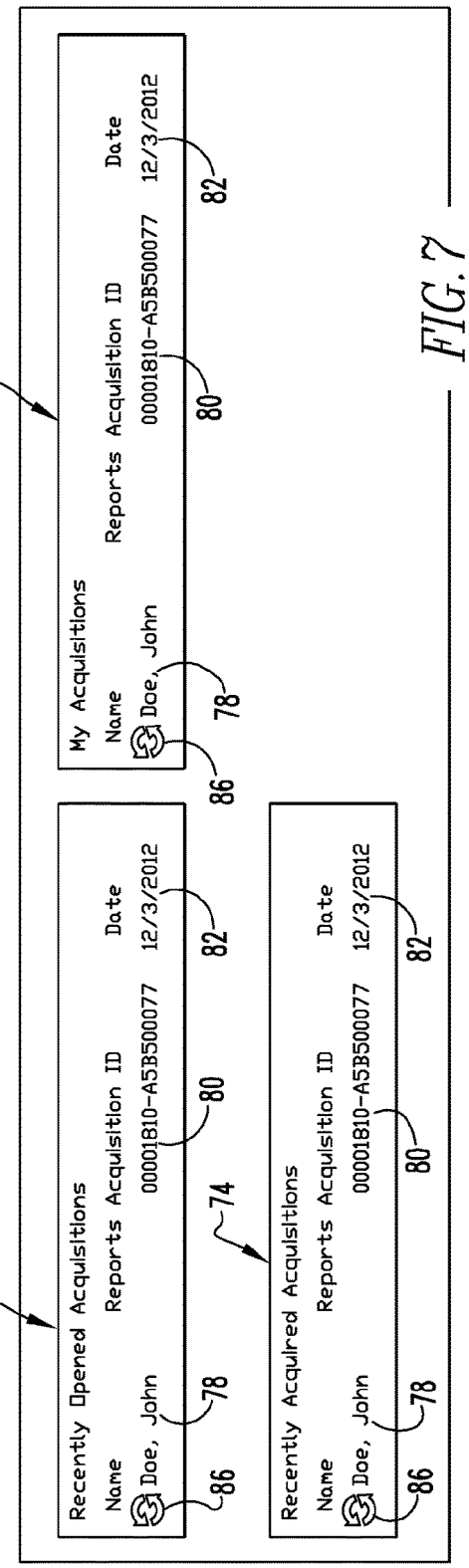
FIG. 7 is a view of a user interface for opening and closing sleep studies according to one exemplary embodiment of the disclosed concept.

FIG. 7 is another view of a user interface for opening sleep studies in accordance with an exemplary embodiment of the disclosed concept. If a user opens a sleep study and updates the sleep study (e.g., a scoring technician scoring a sleep study) the locally stored sleep study files at client 20 will no longer be synchronized with the remotely stored sleep study files at server 32. When the sleep study files are not synchronized, synchronize indicator 86 is shown beside the sleep study indicating that it needs to be synchronized, as shown in FIG. 7. When the sleep study is closed by the user, the method of FIG. 4 is initiated and any new or updated locally stored sleep study files are uploaded to server 32 if a network connection is available. If a network connection is not available, a notification will be displayed to the user and the sleep study will subsequently need to be manually synchronized when a network connection becomes available.

Figure 8A:
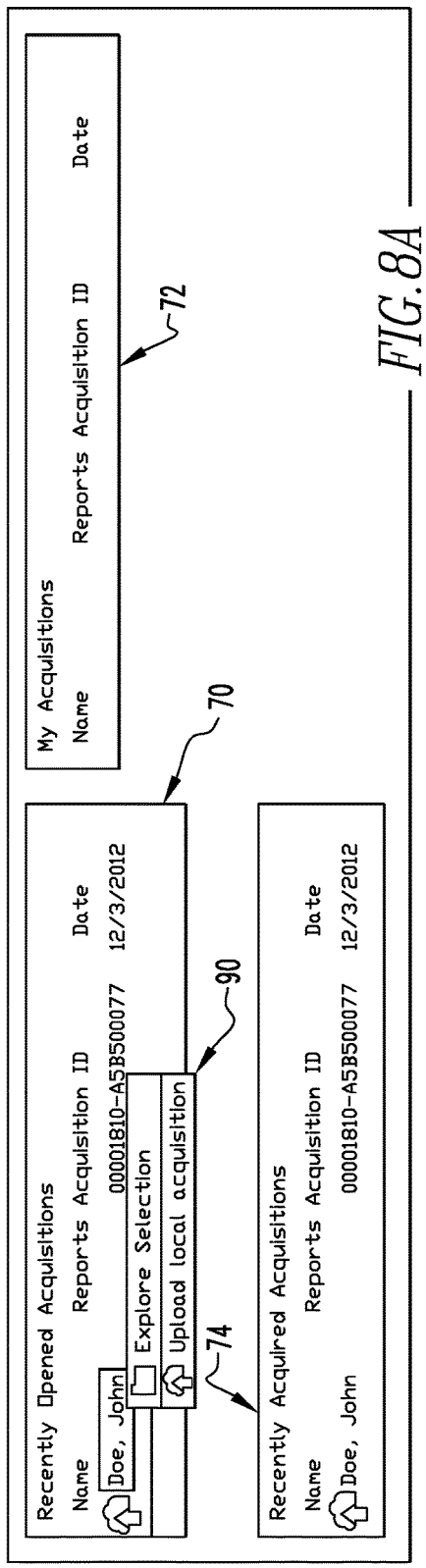
FIGS. 8A and 8B are views of a user interface for opening and closing sleep studies according to one exemplary embodiment of the disclosed concept.
Figure 8B:
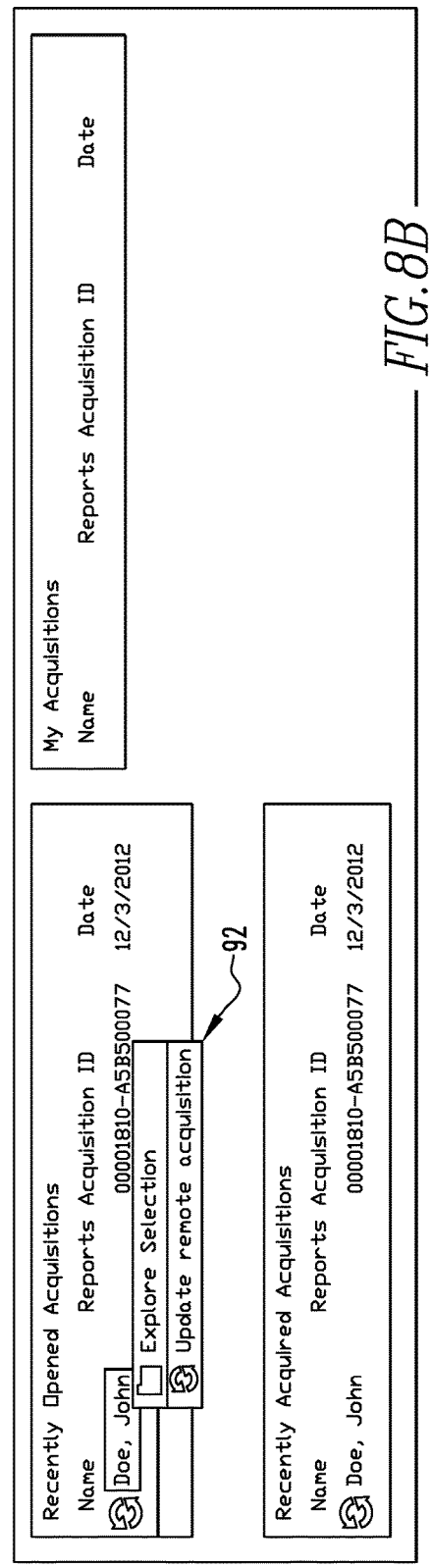

FIGS. 8A and 8B are additional views of a user interface for opening sleep study files. In the case that a network connection was previously not available and a user wants to manually upload (e.g., upload sleep study files from client 20 to server 32 when the sleep study does not exist on server 32) or synchronize (e.g., upload new and updated sleep study files from client 20 to server 32 when the sleep study exists on server 32) sleep study files, the user may manually activate a manual upload menu 90 (see FIG. 8A) or a manual synchronize menu 92 (see FIG. 8B) by, for example, right clicking on the sleep study in the user interface. From the manual upload menu 90, the user can select to upload the locally stored sleep study files to server 32. From the manual synchronization menu, the user can select to synchronize locally stored sleep study files with server 32. It will be appreciated that a user is not limited to initiating a manual upload or synchronization after a failed network connection, but rather the user may initiate a manual upload or synchronization at any time.

Although not shown, it is contemplated that manual upload menu 90, manual synchronize menu 92, or another similarly activated menu may include an option for only downloading report data related to a sleep study. Report data refers to data such as scoring data or any data other than raw sleep study data. The raw sleep study data may include a large amount of data that can take a while to download, whereas the report data could be downloaded more quickly. As a particular user may only be interested in the report data, it would thus be beneficial to give the user the option to just download the report data.

Figure 9:
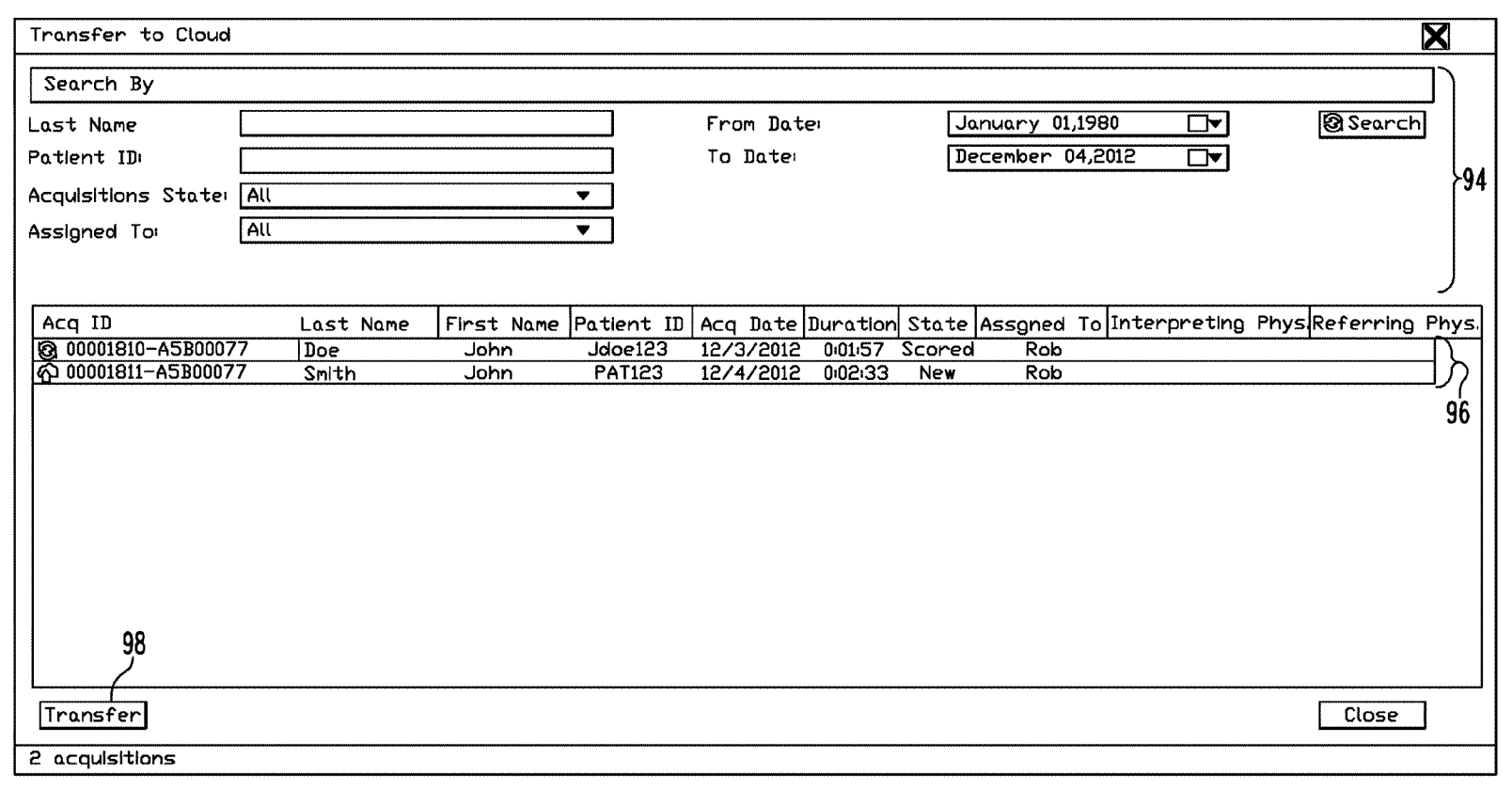

FIG. 9 is a view of a user interface for manually uploading or synchronizing sleep study flies in accordance with an embodiment of the disclosed concept. A search area 94 allows users to search for sleep studies based on various criteria such as, without limitation, user name, patient ID, acquisition state, assigned user, and date. Sleep study display area 96 displays sleep studies that meet the search criteria and need to be updated (e.g., locally stored sleep studies that have new or updated files). Transfer button 98 is activated to upload or synchronize all the sleep studies that are selected in the sleep study display area 96.

Although not shown, it is contemplated that the user interface similar to FIG. 9 can also be used to search for sleep studies for manually downloading or synchronizing local sleep studies. Transfer button 98 may be activated to download entire sleep studies that do not yet exist locally as well as to update local sleep studies that already exist locally and are out of date with server 32.

In addition, it is contemplated that a similar interface can be used to search for studies that should be deleted from server 32. When a sleep study reaches the completed state and no longer needs to be accessed by remote users, it is beneficial to give users a method to delete the sleep study from the server for the purpose of saving space. A delete button may be used to delete sleep studies from server 32.

Although the disclosed concept has been described in the context of transferring sleep study data, it is contemplated that the disclosed concept may also be adapted for use in transferring any type of data between remote locations and a central storage location. It will be appreciated that the disclosed concept is particularly suitable for use in transferring groups of files.

The disclosed concept can also be embodied as computer readable codes on a tangible, non-transitory computer readable recording medium. The computer readable recording medium is any data storage device that can store data which can be thereafter read by a computer system. Non-limiting examples of the computer readable recording medium include read-only memory (ROM), non-volatile random-access memory (RAM), CD-ROMs, magnetic tapes, floppy disks, disk storage devices, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of automatically transferring data between a client and a server, the method comprising:
   downloading a set of data from the server;
   receiving a request to close the set of data at the client;
   determining, in response to the request to close, whether the set of data includes new or updated files, wherein determining whether the set of data includes new or updated files includes determining that any files that have been added to the set of data or have been updated within the set of data since the set of data has been downloaded from the server are the new or updated files in the set of data;
   upon determining that the set of data includes the new or updated files, determining whether a network connection to the server is available;
   if the network connection is available, uploading at least one of the new or updated files in the set of data to the server, otherwise displaying a notification that the at least one of the new or updated files in the set of data have not been uploaded; and
   closing the set of data, wherein the set of data includes sleep study data.

2. The method of claim 1, wherein the request to close the set of data is received through a user interface at the client.

3. The method of claim 2, wherein the user interface includes an indicator structured to indicate whether the set of data at the client is synchronized with the set of data at the server.

4. The method of claim 3, wherein the user interface is structured to display any sets of data that are not synchronized with the server.

5. The method of claim 2, wherein the user interface is structured to allow a user to manually initiate downloading of the set of data.

6. The method of claim 1, wherein the sleep study data includes raw sleep study data and scoring data.

7. The method of claim 1, wherein the new or updated files in the set of data are a subset of the total number of files in the set of data, and wherein uploading at least one of the new or updated files in the set of data to the server includes uploading only the new or updated files in the set of data to the server.

8. A non-transitory computer readable medium storing one or more programs, including instructions, which when executed by a computer, causes the computer to perform a method of transferring data between a client and a server, the method comprising:
   downloading a set of data from the server;
   receiving a request to close the set of data at the client;
   determining, in response to the request to close, whether the set of data includes new or updated files, wherein determining whether the set of data includes new or updated files includes determining that any files that have been added to the set of data or have been updated within the set of data since the set of data has been downloaded from the server are the new or updated files in the set of data;
   upon determining that the set of data includes the new or updated files, determining whether a network connection to the server is available;
   if the network connection is available, uploading at least one of the new or updated files in the set of data to the server, otherwise displaying a notification that the at least one of the new or updated files in the set of data have not been uploaded; and
   closing the set of data, wherein the set of data includes sleep study data.

9. The non-transitory computer readable medium of claim 8, wherein the request to close the set of data is received through a user interface at the client.

10. The non-transitory computer readable medium of claim 9, wherein the user interface includes an indicator structured to indicate whether the set of data at the client is synchronized with the set of data at the server.

11. The non-transitory computer readable medium of claim 10, wherein the user interface is structured to display any sets of data that are not synchronized with the server.

12. The non-transitory computer readable medium of claim 8, wherein the user interface is structured to allow a user to manually initiate downloading of the set of data.

13. A system to automatically transfer data, the system comprising:
   a client device comprising a memory, the client device structured to download a set of data from the server, to receive a request to close the set of data, to determine, in response to the request to close, whether the set of data includes new or updated files, and to close the set of data,
   wherein determining whether the set of data includes new or updated files includes determining that any files that have been added to the set of data or have been updated within the set of data since the set of data has been downloaded from the server are the new or updated files in the set of data, wherein the client is structured to determine whether a network connection is available upon determining that the set of data includes the new or updated files, wherein the client device is structured to upload at least one of the new or updated files in the set of data to a server prior to closing the set of data if the network connection is available, and wherein the client device is structured to display a notification that the at least one of the new or updated files in the set of data have not been uploaded prior to closing the set of data if the network connection is not available, wherein the set of data includes sleep study data.

14. The system of claim 13, wherein the client device is structured to generate a user interface having an indicator structured to indicate whether the set of data at the client is synchronized with the set of data at the server.

15. The system of claim 14, wherein the user interface is structured to display any sets of data that are not synchronized with the server.

16. The system of claim 14, wherein the user interface is structured to allow the user to manually initiate downloading of the set of data.

* * * * *